United States Patent [19]
Tometsko et al.

[11] Patent Number: 5,750,330
[45] Date of Patent: May 12, 1998

[54] METHOD AND COMPOSITION FOR LYOPHILIZING RED BLOOD CELLS

[75] Inventors: Andrew M. Tometsko, deceased, late of Rochester, by Carol R. Tometsko, executrix; Stephen Dertinger, Webster; Dorothea Torous; Kenneth Tometsko, both of Rochester, all of N.Y.

[73] Assignee: Litron Laboratories, Rochester, N.Y.

[21] Appl. No.: 666,134

[22] Filed: Jun. 19, 1996

[51] Int. Cl.$^6$ .................................................. A01N 1/02
[52] U.S. Cl. ......................................... 435/2; 435/1.3
[58] Field of Search ................................ 435/2, 1.3

[56] References Cited

U.S. PATENT DOCUMENTS

| | | | |
|---|---|---|---|
| 4,874,690 | 10/1989 | Goodrich, Jr. et al. | 435/2 |
| 5,043,261 | 8/1991 | Goodrich et al. | 435/2 |
| 5,045,446 | 9/1991 | Goodrich, Jr. et al. | 435/2 |
| 5,171,661 | 12/1992 | Goodrich, Jr. et al. | 435/2 |
| 5,242,792 | 9/1993 | Rudolph et al. | 435/2 |
| 5,340,592 | 8/1994 | Goodrich, Jr. et al. | 424/533 |
| 5,364,756 | 11/1994 | Livesey et al. | 435/2 |
| 5,425,951 | 6/1995 | Goodrich, Jr. et al. | 424/520 |

OTHER PUBLICATIONS

Jones RC, Aust. J. Biol. Sci 22:983–94(1969).
Riazantsev V et al., Ukrainskii Biokhimichskii Zhurnal 59(5):97–9 (1987).

*Primary Examiner*—Sandy Saucier
*Attorney, Agent, or Firm*—Hodgson, Russ, Andrews, Woods & Goodyear

[57] ABSTRACT

Disclosed are a composition for the lyophilization of mammalian red blood cells comprising a hydrophilic polymer, a carbohydrate, and an organic solvent; and a method of using the composition to lyophilize red blood cells comprising mixing red blood cells with the composition, freezing the mixture, and drying the mixture by removing water by sublimation. Also disclosed are red blood cells lyophilized according to this method for lyophilization, and a method for reconstituting the lyophilized red blood cells. In particular, the composition used to lyophilize the red blood cells comprises a mixture of a hydrophilic polymer ranging from 1,450–20,000 Daltons at 5–50% w/v, a mono- or disaccharide or a mixture thereof from 0.01–0.2M and an organic solvent such as a primary alcohol, a secondary alcohol, dimethyl sulfoxide or combinations thereof at 0.5–20% v/v.

19 Claims, 1 Drawing Sheet

METHOD AND COMPOSITION FOR LYOPHILIZING RED BLOOD CELLS

FIELD OF THE INVENTION

This invention is directed to the fields of biochemistry, hematology and cryopreservation. More particularly, the present invention provides a novel composition and use of the composition in a method for the preservation and storage of mammalian red blood cells by lyophilization, and for the reconstitution of red blood cells lyophilized according to the present invention.

BACKGROUND OF THE INVENTION

1. Problems Encountered in Storage of Red Blood Cells

Red blood cells (RBCs) and blood components are quite sensitive to handling and storage conditions. Their integrity during storage depends on a delicate biochemical balance which includes glucose, hydrogen ion (pH) and adenosine triphosphate (ATP) levels. For RBCs, this balance has best been maintained by storing blood at temperatures between 1°–6° C. Depending on collection and storage conditions, blood cells can be maintained in a transfusion-acceptable state for approximately 21–42 days. This short shelf-life makes the national blood supply very sensitive to the pressures of supply and demand. When demand is low, excess blood becomes outdated and is discarded. When demand for donated blood outstrips supply, critical shortages result. In addition to the difficulties of maintaining a threshold supply of transfusable blood for typical short-term needs, it is also desirable to stockpile massive reserves of blood in case of catastrophe. Traditional methods whereby blood is stored in hydrated form at 1°–6° C. are incapable of establishing such reserves.

Freezing cells and other blood products overcomes some of these problems. When RBCs are frozen in the presence of cryoprotective agents such as glycerol and dimethyl sulfoxide, their shelf-life can be increased to years (Sloviter, 1952). While frozen cells can be effectively stockpiled for times when demand exceeds supply, the maintenance of such cells is costly, requiring sufficient freezer space and uninterrupted electrical power. Thus, new methods are needed for storing blood cells and blood components for long periods of time in a more effective and cost efficient manner.

2. Related Art

Methods of lyophilizing (freeze-drying) mammalian red blood cells are known to those skilled in the art. Rudolph et al., in U.S. Pat. No. 5,242,792, provide a process for preparing mammalian red blood cells for dry storage by mixing the RBCs with a protective agent selected from sucrose, raffinose, maltose, lactose, and trehalose; permeabilizing the RBCs with a sugar alcohol selected from inositol and glycerol; agitating the RBC mixture; and lyophilizing the mixture.

Goodrich, Jr., et al., in U.S. Pat. No. 4,874,690, provide a process for the lyophilization of red blood cells by mixing the RBCs with a monosaccharide in a concentration of from about 7 to 37.5% (0.5M to 4M as disclosed in U.S. Pat. No. 5,340,592), an amphipathic polymer (having both hydrophilicity and hydrophobicity) as disclosed in U.S. Pat. No. 5,425,951) having a molecular weight of from about 5K to about 80K and having a concentration of from about 0.7% to saturation level such as polyvinylpyrrolidone or dextran, a polyanion having multiple phosphate, sulfate or carboxlate groups; followed by a freeze-drying step.

Goodrich, Jr., et al., in U.S. Pat. No. 5,171,661, provide a medium for lyophilization of red blood cells by mixing the RBCs including a monosaccharide in a concentration of from about 0.5M to 4M, and an amphipathic polymer having a molecular weight of from about 10K to about 360K and having a concentration of from about of at least 0.1 mM such as polyvinylpyrrolidone or dextran.

Goodrich, Jr., et al., provide a process for the lyophilization of red blood cells by mixing the RBCs with a monosaccharide in a concentration of from about 7.0% to 37.5% (in U.S. Pat. No. 5,045,446) or about 0.5M to 4M (in U.S. Pat. No. 5,340,592), followed by a freeze-drying step. Additionally, process may include an amphipathic polymer of from about 1K to about 360K and having a concentration of from about 0.7% to saturation level (in U.S. Pat. No. 5,045,446) or from about 10K to about 360K and having a concentration of from about 0.1 mM to saturation level (in U.S. Pat. No. 5,340,592).

The above-identified methods result in reconstituted cells which show viability and the ability to transport oxygen. The uses of such cells include use for biochemical research and clinical diagnostic applications. Reconstitution (rehydration) of such cells is typically in an isotonic reconstituting solution such as a phosphate-buffered saline solution containing significant (>15%) sugar concentration or sugar solution and amphipathic polymer. However, there is a need for a method of lyophilizing RBCs such that the lyophilized RBCs can be rehydrated efficiently and in a manner whereby the rehydrated RBCs exhibit (1) high yields, (2) biological function, and (3) tolerance to plasma/serum, which is essential for therapeutic applications.

SUMMARY OF THE INVENTION

The method described herein allows for the lyophilization of RBCs whereby said rehydrated cells exhibit virtually unchanged cellular morphology, enzyme activity, and oxygen-binding characteristics, while being able to maintain cell integrity in an osmotic environment typical for therapeutic uses. The process of dehydration effectively arrests RBC metabolism and provides a dry material which exhibits an extended shelf-life and tolerates a greater range of storage temperatures. Briefly, the process consists of suspending RBCs in a lyophilization formulation comprising a water soluble, synthetic, hydrophilic polymer; a carbohydrate selected from the group of a monosaccharide or disaccharide; and an organic solvent. The cell suspension is then frozen, and water is removed from the material by sublimation.

DETAILED DESCRIPTION OF THE INVENTION

Figure 1:
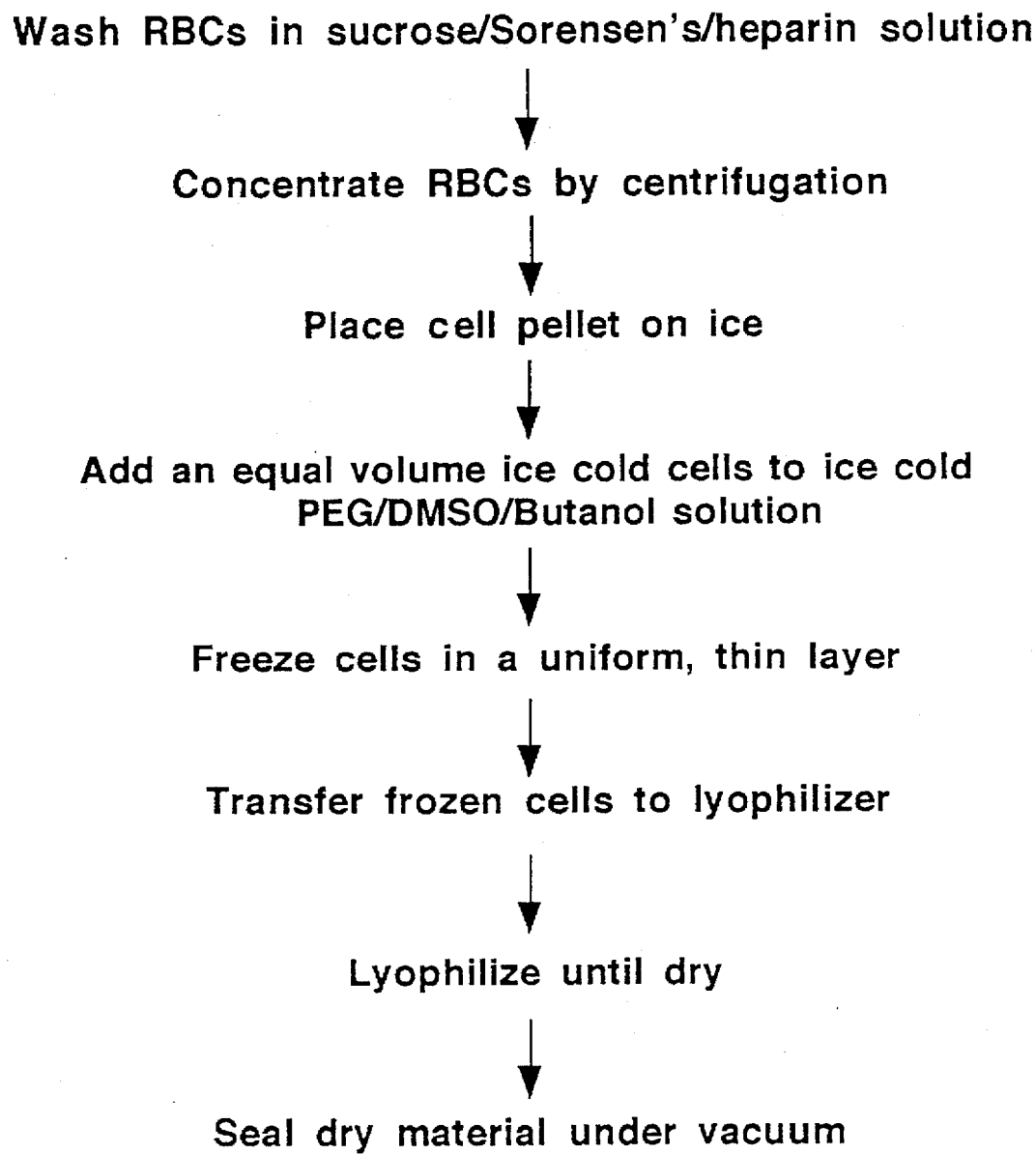
FIG. 1 is a diagrammatic presentation of one embodiment of the method according to the present invention for freeze-drying mammalian red blood cells.

The present invention provides a composition and method for using the composition to lyophilize RBCs whereby said rehydrated cells exhibit virtually unchanged cellular morphology, enzyme activity, and oxygen-binding characteristics as compared to untreated RBCs. Further, RBCs lyophilized with the composition and according to the method of the present invention can be stabilized to maintain cell integrity in an osmotic environment typical for therapeutic uses. The composition of the invention involves the use of a water soluble, hydrophilic polymer; a carbohydrate selected from the group of a monosaccharide or disaccharide; and an organic solvent. By the term "composition" is meant, for the purposes of the specification and claims to refer to the solution and components contained in that solution used for suspending the RBCs in a method for lyophilizing RBCs.

A hydrophilic polymer useful as a component in the composition of the present invention would desirably have the following properties: (i) is highly water soluble, thereby can be used in a wide range of concentrations; (ii) forms a stable, non-collapsing matrix during lyophilization; and (iii) is nontoxic in humans. A preferred hydrophilic polymer is polyethylene glycol (PEG). Other hydrophilic polymers which may be used with the invention are selected from the group consisting of dextran, hydroxyethyl starch, and polyoxyethylene-23-lauryl ether. The use of PEG as an extracellular cryoprotectant has been described previously (Neronov et al., 1992, *Cryobiology*, 29:296–299). When cooled, PEG forms a glassy state which protects cells from damage due to osmotic forces and ice crystal formation during freezing.

It is an unexpected result that a non-collapsible matrix of PEG also protects fragile erythrocyte membranes and ensures good cell morphology and high cell recovery upon lyophilization and subsequent rehydration. Experiments described herein indicate that the hydrophilic polymer such as PEG can range in molecular mass from about 1,450 daltons to about 20,000 daltons and be effective at protecting cellular membranes and their integrity during lyophilization. Also, the hydrophilic polymer can vary in effective concentrations in the composition, ranging from about 5% to 50% weight/volume. Note that all hydrophilic polymer concentrations which appear herein are expressed as percent weight/volume (% w/v).

While a hydrophilic polymer is shown herein to be very effective at protecting RBC membranes and ensuring high cell recovery through the process of lyophilization and subsequent reconstitution, other measures are required to protect hemoglobin (Hb), the oxygen-carrying component of the erythrocyte. The oxygen-binding portion of Hb, or heme groups, are essentially porphyrin structures with a centrally bound iron (Fe) atom. Under normal, physiological conditions, these iron atoms remain in the ferrous [Fe(II)] oxidation state whether or not heme has bound an oxygen molecule at the 6th liganding position. The FE(II) of heme can be oxidized to FE(III) to form methemoglobin (MetHb). MetHb is not clinically useful for transfusion, since it does not carry oxygen [its FE(III) is already coordinated with a water molecule at the 6th liganding position]. A significant challenge associated with freeze-drying RBCs for clinical use is to recover Hb which has not been oxidized to Fe(III), but rather retains its normal, reversible oxygen-binding character.

In this regard, carbohydrates have been found to have a protecting effect on dry Hb (Labrude et al., 1980, *J. Pharm. Pharmacol.* 32:588–589). In the composition of the present invention, the function of the hydrophilic polymer such as PEG is improved by adding a carbohydrate to protect freeze-dried Hb's oxygen-carrying character. While the carbohydrates which provide such protection in the method of the present invention are chosen from a group of monosaccharides and disaccharides, a preferred carbohydrate is a hexose-pentose disaccharide such as sucrose. It is an unexpected result that a disaccharide was found to exhibit significantly more of a protective effect than the monosaccharides tested in the composition and method according to the present invention, since disaccharides do not ordinarily permeate the RBC membrane to an appreciable extent. In the composition and method according to the present invention, the carbohydrate exerts a maximum protecting effect when present at a final concentration of about 0.01M to about 0.2M with a preferred range of from about 0.01M to about 0.1M. It is also an unexpected result that the carbohydrate is most effective at a concentration of less than 200 mM, as other methods for lyophilizing RBCs typically teach a carbohydrate concentration of 300 mM to 4M.

There are two modes by which the carbohydrate may be added in becoming a component to the composition according to the present invention. As will be appreciated by the more detailed description which follows, in one mode the carbohydrate is contained in the buffered wash solution used in the isolation of the RBCs. While the supernatant from such a wash is removed, it is appreciated by those skilled in the art that residual buffered solution is trapped between and surrounding the RBCs of the pellet. Thus, the residual buffered solution can contain an effective amount of carbohydrate, which when added with the RBCs, becomes the carbohydrate component in the composition of the present invention. Alternatively, the carbohydrate may be added as a component to the composition before the addition of the RBCs to be suspended and lyophilized. In this variation of the embodiment, it is not contemplated that the buffered solution used to wash the RBCs contains any carbohydrate or a concentration of carbohydrate required for the method according to the present invention.

It was found in the composition and method according to the present invention, that addition of certain organic solvents, in combination with the carbohydrate additive, helped to stabilize intercellular Hb during lyophilization and subsequent storage. Organic solvents found to be useful in the method of the present invention are chosen from a group consisting of primary alcohols, secondary alcohols, or dimethyl sulfoxide (DMSO). In a preferred embodiment, the alcohol which has shown particular suitability is 1-butanol. In an additional embodiment, a combination of an alcohol and DMSO is used. Experiments described herein suggest that the protecting effects of DMSO and alcohol are additive. Thus, DMSO and alcohol may each be included in a composition for lyophilization of RBCs according to the present invention. Whether as separate additives, or when combining DMSO and alcohol together, the total organic solvent component should be present in the composition in a concentration range of from about 0.5% to about 20% volume/volume (v/v) with a preferred range of from about 1% to about 10% v/v. By the term "an organic solvent" is meant, for the purposes of the specification and claims to refer to at least one species of organic solvent and encompasses a combination of different species of organic solvents selected from the group consisting of primary alcohols, secondary alcohols, or dimethyl sulfoxide.

Thus, in one embodiment of the present invention, the composition for lyophilizing mammalian RBCs comprises a water soluble, synthetic, hydrophilic polymer; a sugar selected from the group of a monosaccharide or disaccharide; and an organic solvent. A method of using the composition to lyophilize RBCs comprises suspending the RBCs in a solution containing a hydrophilic polymer having a molecular mass of from about 1,450 to about 20,000 daltons in a concentration of from about 5% to about 50% w/v, a carbohydrate selected from the group consisting of monosaccharides and disaccharides or a combination thereof which is present in the solution in a concentration of from about 0.01M to about 0.2M, and an organic solvent in a concentration range of from about 0.5% to about 20% v/v.

The suspension is frozen using methods known in the art, and then the RBCs are dried by sublimation of the water using methods known to those skilled in the art.

The composition of the present invention can further comprise additive components which enhance the functionality of one or more of the hydrophilic polymer, the carbohydrate, and the organic solvent. There are factors such as the density (number) of RBCs to be lyophilized, the duration of the freezing process and the temperatures employed in that process, and other factors which can vary in a method for lyophilization of RBCs. Thus, the composition of the present invention may be altered slightly to take into account such variables.

For example, when mammalian RBCs are frozen and subsequently lyophilized at relatively high cell densities (i.e., $>5 \times 10^7$ RBCs/ml), the presence of salts in the lyophilization medium should be considered to minimize cell-cell aggregation that may occur at such densities. Thus, in one embodiment of the present invention, the composition may further comprise phosphate salts. Chloride salts are not desirable as they tend to promote aggregation of RBCs. Thus, by the term "salt" is meant, for the purposes of the specification and claims to refer to a salt having a low chloride ion concentration (0 mM to 25 mM chloride) such as $KH_2PO_4$, $Na_2HPO_4$, and a combination of $KH_2PO_4$ and $Na_2HPO_4$ (primary components of a solution commercially available as Sorensen's buffer).

There are two potential sources of salts that can be used in conjunction with the method according to the present invention. A first source of salts is the buffer used in the isolation of the RBCs. As known to those skilled in the art, a preferred method for obtaining RBCs for lyophilization comprises preparing RBCs from a whole blood sample by centrifugation, removing the plasma supernatant, washing the RBCs at least once in a buffered solution, wherein the washed RBCs are pelleted by centrifugation before being suspended in a composition for lyophilization. While the supernatant from such a wash is removed, it is appreciated by those skilled in the art that residual buffered solution is trapped between and surrounding the RBCs of the pellet. When the wash solution is chosen carefully, and is characterized by a low chloride ion concentration, there is no need to remove these residual salts.

A second source of salts that may be used is adding salt as a component to the composition before the addition of the RBCs to be suspended and lyophilized. In this variation of the embodiment, it is not contemplated that the buffered solution used to wash the RBCs contains the salt. Rather, the composition in which the RBCs are suspended and then lyophilized comprises a hydrophilic polymer, one or more carbohydrates, an organic solvent, and further comprises a salt. Since the polymer, such as PEG, exerts an osmotic force on RBCs which is well tolerated, the need for salts in the composition for lyophilizing RBCs is not required to preserve osmotic balance and cell integrity. Rather, salts of low chloride ion concentration may be useful when lyophilizing RBCs at relatively high cell densities to facilitate the recovery of unaggregated RBCs upon reconstitution. Whether the salt is added by the presence of residual buffered wash solution or as part of the composition before the RBCs are added, an effective concentration of the salt may range from about 5 mM to about 150 mM, depending on the formulation of the salt used.

To further increase the yield of single, unaggregated cells upon lyophilization and reconstitution, the composition may further comprise anti-aggregant agents. One or more anti-aggregants may be present in the buffered wash solution and added as a component to the composition by the presence of residual buffered wash solution contained in the RBC preparation to be lyophilized, or as part of the composition before the RBCs are added. Such anti-aggregants may be selected from the group consisting of a citrate-phosphate-dextrose solution (commercially available as CPD); CPD with adenine (commercially available as CPD-A); or heparin. Depending on the anti-aggregant selected, the effective concentration of the anti-aggregant in the composition will vary. For example, an effective concentration of CPD or CPD-A in the composition ranges from about 5% to about 15% v/v, and an effective concentration of heparin in the composition ranges from about 10 USP units/ml to about 1000 USP units/ml. As illustrated in Example 2 herein, in lyophilization of relatively high cell densities of RBCs, the recovery of single, unaggregated cells is improved by supplementing the composition with these anti-aggregant agents.

Thus, in another embodiment of the present invention, the composition for lyophilizing mammalian RBCs in a relatively high cell density comprises a water soluble, synthetic, hydrophilic polymer; a sugar selected from the group of a monosaccharide or disaccharide; an organic solvent; and further comprises a salt and/or an anti-aggregant. A method of using the composition to lyophilize RBCs in a relatively high cell density comprises suspending the RBCs in a solution containing a hydrophilic polymer having a molecular mass of from about 1,450 to about 20,000 daltons in a concentration of from about 5% to about 50% w/v, a carbohydrate selected from the group consisting of monosaccharides and disaccharides or a combination thereof which is present in the solution in a concentration of from about 0.01M to about 0.2M, an organic solvent in a concentration range of from about 0.5% to about 20% v/v, and an anti-aggregant such as CPD or CPD-A in a concentration range of from about 5% to about 15% v/v or heparin in a concentration of from about 10 USP units/ml to about 1000 units/ml. The suspension is frozen using methods known in the art, and then the RBCs are dried by sublimation of the water using methods known to those skilled in the art.

Methods for reconstituting red blood cells lyophilized according to the method of the present invention using the composition of the present invention are provided which minimize cell-cell aggregation and maximize cell recovery and biological activity.

Having described different embodiments of the present invention, the following examples are provided to illustrate specific applications of the invention but are not intended to limit the scope of the invention described in this application.

EXAMPLE 1

Effect of Molecular Mass and Concentration of the Hydrophilic Polymer Component of the Composition A hydrophilic polymer may be included as a component of the composition according to the present invention, in a range of molecular sizes and concentrations. Experiments were performed to demonstrate the molecular weights and concentrations of the hydrophilic polymer which are particularly suitable for protecting RBCs through the process of lyophilization. PEG was chosen as an exemplary, and preferred, hydrophilic polymer.

For this determination, human blood was drawn from a healthy volunteer and collected into 0.9% NaCl containing 500 USP units heparin/ml. Glutaraldehyde-fixed yeast particles which had been labeled with fluorescein were added to the blood suspension. Flow cytometry was used to measure the ratio of fluorescent yeast particles to red blood cells before and after freeze-drying. In this manner, yeast particles served as an internal standard for evaluating RBC recovery. Separate sample tubes contained a PEG of a different molecular size, and each was evaluated over a range of PEG concentrations. Aliquots of the RBC/yeast suspension were added. Specifically, 30 μl aliquots were added to tubes containing 300 μl PEG in a final concentration of either 5%, 10%, 20%, 30%, 40%, or 50% w/v and varying in molecular sizes of 1000, 1450, 3350, 8000, 10000 or 20000 daltons (prepared in dH$_2$O). The density of the RBCs in each of the lyophilization solution suspensions was determined to be 2.7×10$^7$ cells/ml. After 5 minutes on ice, the blood samples were moved to a −70° C. freezer and frozen in a uniform, thin layer. After 1 hour, the frozen samples were transferred to a lyophilizer operating at 100 microns of member (Hg) with an internal chamber temperature of about −90° C. Sample vials were kept under vacuum until they were dry (i.e. until a residual water content of <3% was achieved).

The dry samples were each reconstituted with 1 ml cold (4° C.) rehydration buffer (10 parts 15% PEG 3350 daltons in dH$_2$O plus 1.4 parts CPD solution). The samples were analyzed by flow cytometry thereby allowing for detection of intact cells. Percent recovery was determined by comparing the RBC/yeast ratio of each sample to that of the initial (untreated) cell suspension. The results are described in Table 1.

TABLE 1

| PEG Molecular Size | Conc. (% w/v) | % Recovery |
| --- | --- | --- |
| 1,000 | 5–50 | 0 |
| 1,450 | 5 | 57 |
|  | 10 | 84 |
|  | 20 | 90 |
|  | 30 | 89 |
|  | 40 | 84 |
|  | 50 | 86 |
| 3,350 | 5 | 60 |
|  | 10 | 85 |
|  | 20 | 87 |
|  | 30 | 86 |
|  | 40 | 82 |
|  | 50 | 86 |
| 6,000 | 5 | 68 |
|  | 10 | 84 |
|  | 20 | 83 |
|  | 30 | 84 |
|  | 40 | 89 |
|  | 50 | 70 |
| 8,000 | 5 | 63 |
|  | 10 | 77 |
|  | 20 | 87 |
|  | 30 | 93 |
|  | 40 | 93 |
|  | 50 | 74 |
| 10,000 | 5 | 28 |
|  | 10 | 69 |
|  | 20 | 85 |
|  | 30 | 99 |
|  | 40 | 83 |
|  | 50 | 88 |
| 20,000 | 5 | 78 |
|  | 10 | 89 |
|  | 20 | 89 |
|  | 30 | 88 |
|  | 40–50 | too viscous |

These data indicate that a hydrophilic polymer such as PEG can protect fragile erythrocyte membranes and cell structural integrity from the rigors of lyophilization and rehydration. The hydrophilic polymer, such as PEG, may be present at a concentration of from about 5% to about 50% w/v. The average molecular mass of the hydrophilic polymer, such as PEG, can range from about 1450 to about 20,000 daltons. As can be seen from Table 1, the optimal concentration of hydrophilic polymer will vary depending on the molecular mass of the hydrophilic polymer selected.

EXAMPLE 2
RBC Washing Solution

In this example is illustrated a salt or an anti-aggregant, added as a further component to the composition by the presence of residual buffered wash solution contained in the RBC preparation of a relatively high cell density to be lyophilized. It was found in the development of the method according to the present invention that there is considerable latitude as to concentration of salts in the composition when lyophilizing human RBCs at relatively low cell densities (i.e., <5×10$^7$ RBCs/ml). At relatively low cell densities, unbuffered salt solutions (e.g., 0.9% NaCl or 0.9% KCl) or buffered salt solutions (e.g. phosphate buffered saline) were found to be acceptable as components in the composition. The latitude of the buffer composition is made apparent by the observation that given a threshold level of the hydrophilic polymer, such as PEG, little or no salts are required to prevent osmotic lysis. Since such a hydrophilic polymer exerts an osmotic pressure on RBCs which is well tolerated over a wide range of concentrations (preferably from about 10% to about 50% w/v), the need for physiological salt concentrations in the composition for lyophilizing RBCs is not required.

In contrast, when RBCs are freeze-dried at relatively high cell densities, the concentration and type of salts in the composition of the present invention should be chosen carefully in order to minimize the extent of cellular aggregation. Since RBCs are typically washed and maintained in solutions which contain salts, significant amounts of salt could be introduced to the composition when washed RBCs are added. Thus, for example, certain salt solutions are not recommended for use as a buffered wash solution before using the composition and method according to the present invention. That is, certain salt solutions used as a buffered wash solution in preparing the RBCs for lyophilization according to the method of the present invention, may result in excessive aggregation of the RBCs prior to the sublimation phase. For instance, when an equal volume of a relatively high density RBCs in 150 mM NaCl is delivered to an equal volume of 40% PEG 3350 daltons, extensive aggregation results. Thus, being alerted to the potential of salt concentrations and types that may tend to promote cell-cell aggregation, one skilled in the art would appreciate that certain options can be made to minimize the potential occurrence of such aggregation.

One option is that if a wash buffer solution such as 150 mM NaCl is used to wash RBCs prior to lyophilization according to the method of the present invention, then aggregation can be minimized by additional dialysis or centrifuging steps with a wash buffer of a lower concentration of salt and/or low in chloride ion concentration. Another option is to replace the initial wash buffer solution such as 150 mM NaCl, with a wash buffer solution of a lower concentration of salt and/or low in chloride ion concentration (e.g. Sorensen's buffer).

In that regard, a variety of salts and/or sugars were tested with a hydrophilic polymer solution such as PEG to assess the extent of cellular aggregation associated with such combinations. Initially, microscopic inspection was utilized to assess the extent of cellular aggregation associated with each combination. The results of these experiments indicated, for example, that cellular aggregation is minimized when the hydrophilic polymer solutions are low in chloride ion concentration. For instance, the least amount of aggregation was observed for PEG solutions in combination with a residual buffered wash solution containing sugars or Sorensen's buffer. An exemplary buffered wash solution consists of both sucrose and Sorensen's buffer. Sucrose present at a concentration of 0.2M in the buffered wash solution provides well-tolerated osmotic conditions and Sorensen's salts provide a physiological pH with a good buffering capacity.

While sucrose/Sorensen's buffer outperformed other RBC washing solutions, further experiments indicated that unacceptable levels of aggregation may still occur at very high densities of RBCs. Therefore, it may be desirable to take additional measures to prevent aggregation. One such additional measure, as described herein below, is the inclusion of an anti-aggregant in the buffered wash solution which can further aid the recovery of single, unaggregated cells after reconstitution from lyophilization according to the method of the present invention.

To illustrate this embodiment, human blood was collected into 0.2M sucrose prepared in Sorenson's buffer (sucrose/Sorensen's buffer) supplemented with either CPD-A (1.4 parts CPD-A to 10 parts buffer) or heparin (1000 units/ml). The cells were concentrated by centrifugation and fluorescent yeast were added to serve as an internal standard for assessing RBC recovery. Sucrose/Sorensen's buffer supplemented with either CPD-A or heparin was used to prepare several cell/yeast suspensions covering a range of cell densities. The cells were placed on ice. Aliquots of the cell/yeast suspension (50 µl) were added to tubes containing 100 µl ice cold 30% PEG 20,000 daltons. After 5 minutes on ice, the samples were frozen and then lyophilized until dry as described above.

The dry blood samples were reconstituted with 1.5 ml cold rehydration buffer. The resulting cell suspensions were analyzed with a flow cytometer. The yield of single cells was derived from the ratio of cells to yeast particles relative to a control sample which was not freeze-dried. The results are described in Table 2.

TABLE 2

| Anticoagulant | Cell Density (cells/ml) | % Cell Recovery |
| --- | --- | --- |
| CPD-A | $1.56 \times 10^8$ | 98 |
| CPD-A | $1.56 \times 10^9$ | 42 |
| Heparin | $2.1 \times 10^8$ | 98 |
| Heparin | $2.1 \times 10^9$ | 94 |

These data indicate that human RBCs can be freeze-dried at very high cell densities in a composition comprising a hydrophilic polymer, a disaccharide, and an anti-aggregant, wherein the composition is low in chloride ions. The anticoagulant heparin, as compared to CPD-A, may be used to a particular advantage where the cell density is very high, and should be present at a concentration of ranging from about 10 to about 1000 USP units/ml.

EXAMPLE 3
Temperature During Sublimation

The primary force which drives the sublimation process is the pressure differential between the product and the condenser of the freeze-dryer created by their temperature differential. The temperature at the location of the condenser and the product are consequently of critical importance. In order to demonstrate effective temperature conditions, an experiment was performed whereby frozen RBCs were maintained over a range of temperatures during lyophilization. Microscopic inspection of cell morphology and measurements of oxyHb recovery were utilized to evaluate the quality of the resulting dry material.

In this experiment, human RBCs were collected into 0.2M sucrose prepared in Sorensen's buffer with 100 USP units heparin/ml. The cells were centrifuged and the supernatant decanted. The pellet of concentrated cells was placed on ice. Aliquots of the ice cold cell suspension (150 µl) were then added to tubes with an equal volume of ice cold 40% PEG 3350 daltons prepared in dH$_2$O (de-ionized water). After 5 minutes on ice, the samples were placed in a $-70°$ C. freezer and frozen in a uniform, thin layer. The frozen samples were transferred to a lyophilizer with a condenser chamber temperature of approximately $-90°$ C. whose vacuum was operating at 100 microns Hg. The samples were maintained at either room temperature (approximately 25° C.), $-4°$ C. or $-30°$ C. until dry.

Immediately after breaking the vacuum a small fraction of the dry material was removed, reconstituted with rehydration buffer and inspected microscopically. The sample was brought up to 2.5 ml with a reagent for measuring oxyhemoglobin (Hemox Solution™) which was supplemented with a nonionic detergent (P-40) in order to lyse the cells. The samples were evaluated spectrophotometrically for percent oxyhemoglobin content. Illustrated in Table 3 is the effect of various temperatures during lyophilization on the preservation of RBCs, presented as a percentage of untreated (control) blood oxyHb content.

TABLE 3

| Temp (°C.) | % oxyHb Recovery | Aggregation |
| --- | --- | --- |
| Control | 100 | none |
| 25° | 82 | extensive |
| $-4°$ | 91 | slight |
| $-30°$ | 100 | none |

These data indicate that the quality of Hb can be maintained and the extent of cellular aggregation minimized by keeping frozen blood at a temperature less than $-4°$ C. over the course of sublimation. In addition to the differences in % oxyHb recovery and aggregation expressed in Table 3 above, it is worth noting that the consistency of the dry material is quite different over this range of temperature differentials. While the dry material at 25° C. was hard and granular, the material at $-30°$ C. was of a powdery, talc-like consistency.

EXAMPLE 4

Characterization of Enzyme Activity

The viability of RBCs which have been reconstituted following a lyophilization process can be characterized by measuring one or more of a number of parameters including cell integrity (Example 1); oxyHb or metHb values (oxyHb, Example 3); and RBC enzyme activity. Regarding the latter, the glucose-6-phosphate dehydrogenase (G6PD) activity of human RBCs was measured before and after lyophilization. In this manner, G6PD served as a model enzyme to demonstrate the conditions whereby biological activity is preserved upon lyophilization and subsequent rehydration. G6PD is an important enzyme which catalyzes the oxidation of glucose-6-phosphate to 6-phosphogluconate with the simultaneous reduction of nicotine adenine dinucleotide phosphate (NADP) to reduced NADP (NADPH). In a second consecutive oxidation reaction, 6-phosphogluconate is converted to 6-phosphogluconolactone, with the reduction of a further molecule of NADP to NADPH. The simultaneous release of $CO_2$ drives the reaction to the right, so in practice, the pathway is not reversible. The assay for G6PD activity entails following the rate of NADPH production which, unlike NADP, has a peak of ultraviolet light absorption at 340 nm (Dacie et al., 1995, in *Practical Haematology*, 8th Edition, pp.233–235).

For this experiment, human RBCs were collected into a solution of 0.2M sucrose prepared in Sorensen's buffer with 100 USP units of heparin/ml. The cells were concentrated by centrifugation and placed on ice. A 150 µl aliquot of the ice cold cell suspension was added to a tube containing an equal volume of ice cold solution of 40% PEG 3350 daltons. After 5 minutes on ice, the sample was frozen in a uniform, thin layer. The frozen sample was transferred to a lyophilizer and dried.

The dry material was lysed with the addition of 0.95 ml $dH_2O$. A 100 µl aliquot of the lysate was evaluated for G6PD activity in quartz cuvettes containing 0.8 ml of a reaction buffer (20 mM Tris-HCl, 0.055 µM $Na_2EDTA$, 10 µM $MgCl_2$ and 0.2 µM NADP). The reaction was initiated through the addition of 100 µl 6 mM glucose-6-phosphate and absorbance at 340 nm was recorded over time. Table 4 illustrates the measured G6PD activity.

TABLE 4

| Sample | Rate of NADPH Formation (ΔAbs./time) | Relative G6PD Activity (%) |
| --- | --- | --- |
| Control | 1.15 | 100 |
| Freeze-dried | 1.10 | 96 |

The accumulation of NADPH indicates that virtually all G6PD activity is retained upon freeze-drying and subsequent rehydration using the composition and method of using the composition according to the present invention.

EXAMPLE 5
Carbohydrate Component of the Composition

Experiments were performed to demonstrate the relative effectiveness of various carbohydrates which may be a component of the composition according to the present invention. To illustrate this embodiment, the carbohydrates were added as a component in forming the composition prior to the addition of the RBCs to be lyophilized. Thus, the buffered wash solution used to wash the RBCs had no appreciable carbohydrate concentration.

Blood was drawn from a healthy volunteer and collected into a 0.9% NaCl solution with+500 USP units heparin/ml. The red blood cells were centrifuged, washed with saline, and placed on ice. Aliquots of the suspension (20 µl) were transferred to tubes containing 200 µl of an ice cold solution containing 20% PEG 3350 daltons, 2.5% DMSO, and the carbohydrate concentration was varied from no added carbohydrate to 0.2M of one the following carbohydrates: sucrose, fructose, glucose, mannitol, sorbitol, trehalose, arabinose, or ribose. The density of these cell suspensions was determined to be $5 \times 10^7$ cells/ml. After 5 minutes on ice, the cell suspensions were frozen in a thin layer at −70° C. and subsequently lyophilized until they were thoroughly dry (vacuum at 100 microns Hg).

Within 60 minutes of breaking the vacuum, the samples were rehydrated with a reagent for determining oxyHb concentration and lysed with non-ionic detergent (P40). The samples were then evaluated spectrophotometrically for % oxyHb content. Illustrated in Table 5 is the effect of various carbohydrates during lyophilization on the preservation of RBCs, presented as a percentage of untreated (control) blood oxyHb content.

TABLE 5

| Carbohydrate | % oxyHb Recovery |
| --- | --- |
| Control (no freeze dry) | 100 |
| Freeze dried with: | |
| O carbohydrate | 80 |
| arabinose | 85 |
| fructose | 95 |
| glucose | 91 |
| mannitol | 80 |
| ribose | 80 |
| sorbitol | 74 |
| sucrose | 99 |
| trehalose | 85 |

When RBCs are lyophilized in a hydrophilic polymer solution such as PEG without any carbohydrate present, Hb is converted to species which do not effectively bind oxygen (e.g. MetHb). Carbohydrate supplements added to the lyophilization medium have been found to improve oxyHb recovery when RBCs are lyophilized and subsequently rehydrated. The data presented in Table 5 indicate that considerable flexibility exists as to the chemical structure of the carbohydrate protectant, as improved oxyHb recovery was observed for samples supplemented with pentose or hexose monosaccharides as well as hexose-hexose or hexose-pentose disaccharides. Further experiments demonstrated that preferred carbohydrates, showing particular effectiveness with the composition and method according to the present invention, include sucrose, glucose and fructose at a preferred final concentration in the composition of about 0.01 to about 0.1M. To those skilled in the art, it is apparent that more than one carbohydrate may be used in the composition, provided the total carbohydrate is in a preferred final concentration in the composition of about 0.01 to about 0.1M.

EXAMPLE 6
Organic Solvent as a Component in the Composition

Experiments were performed to demonstrate the relative protecting effect that certain organic solvents have, when included as a component in the composition, on RBCs lyophilized according to the method of the present invention. Human RBCs were washed with sucrose/Sorensen's buffer with 100 units heparin/ml. The pellet of cells was placed on ice. Aliquots of the cell suspension (150 µl) were transferred to tubes with 150 µl ice cold solution of PEG 3350 daltons (40%) with each one of the following solvents at 10% (v/v): dimethyl sulfoxide (DMSO); 1-butanol; 1-octanol; acetone; methylethyl ketone; tetrahydrofuran; methanol; isopropyl alcohol and ethyl ether. After 5 minutes on ice, the cell suspensions were frozen in a thin layer at −70° C. and lyophilized until dry (vacuum at 100 microns Hg).

The dry samples were stored for 24 hours at less than ideal conditions so that any protecting effects offered by the organic solvent component would be discerned more rapidly. Specifically, the samples were maintained at room temperature in containers which were open to the atmosphere. After 24 hours, each sample was rehydrated with a reagent for measuring oxyHb and lysed with a non-ionic detergent. The samples were then evaluated spectrophotometrically for % oxyhemoglobin recovery. Protective effects of an organic solvent, when included as a component in the composition and method for lyophilizing RBCs according to the present invention, are presented in Table 6 as a percentage of control blood which was not freeze-dried, but rather analyzed immediately for oxyHb content.

TABLE 6

| Organic solvent | % oxyHb Recovery |
|---|---|
| Freeze-dried with: | |
| ethyl ether | 58 |
| no organic solvent | 61 |
| methanol | 61 |
| acetone | 61 |
| methylethyl ketone | 62 |
| 1-octanol | 66 |
| isopropyl alcohol | 72 |
| dimethyl sulfoxide | 85 |
| 1-butanol | 95 |

When the composition containing a hydrophilic polymer and one or more carbohydrates is modified to also contain organic solvents, oxyHb recovery is improved. Thus, the presence of an organic solvent in the composition enhances the protective effect of the composition when used in the method for lyophilizing RBCs according to the present invention. Further experiments demonstrated that preferred organic solvents, showing particular effectiveness with the composition and method according to the present invention, include primary alcohols, secondary alcohols, or dimethyl sulfoxide (DMSO) at a preferred final concentration in the composition of from about 1% to about 10% v/v. Also, more than one organic solvent may be used in the composition, provided the total organic solvent is in a preferred final concentration in the composition of from about 1% to about 10% v/v.

EXAMPLE 7

Dimethyl Sulfoxide as a Component in the Composition

In one preferred embodiment of the invention, the organic solvent contained in the composition according to the present invention comprises dimethyl sulfoxide (DMSO). Experiments were performed to demonstrate the effective concentration range of DMSO in the composition. Human RBCs were collected into a 10 ml solution of 0.2M sucrose prepared in Sorensen's buffer with 100 USP units of heparin/ml. The cells were centrifuged, the supernatant was decanted, and the pellet was placed on ice. Aliquots of the ice cold cell suspension (100 μl) were added to tubes with an equal volume of ice cold solution of 40% PEG 3350 daltons with either 0%, 1% or 5% DMSO for final DMSO concentrations of 0, 0.5 or 2.5% v/v, respectively. After 5 minutes on ice, the samples were placed in a freezer (−70° C.) and frozen in a thin layer. The frozen samples were transferred to a lyophilizer and freeze-dried. Immediately after breaking the vacuum, the vials of freeze-dried material were capped with a butyl rubber stopper and flushed with $N_2$. These samples were kept at room temperature for 30 minutes before they were rehydrated with a reagent for measuring oxyHb and lysed with a non-ionic detergent. Each lysate was analyzed spectrophotometrically and the percent oxyhemoglobin recovery was calculated relative to a control blood lysate which was not freeze-dried. Illustrated in Table 7 is the effect of various concentrations of DMSO on lyophilization of RBCs.

TABLE 7

| Final DMSO Conc.(%) | % oxyHb Recovery |
|---|---|
| 0 | 59 |
| 0.5 | 75 |
| 2.5 | 100 |

The results indicate that red blood cells which are freeze-dried according to the method of the present invention resist oxidative damage and continue to bind oxygen in a cooperative manner when the composition contains DMSO at a concentration of from about 0.5% to about 2.5%, and at a preferred concentration of about 2.5%.

EXAMPLE 8

1-Butanol as a Component in the Composition

In one preferred embodiment of the invention, the organic solvent contained in the composition according to the present invention comprises 1-butanol. Experiments were performed to demonstrate the effective concentration range of 1-butanol in the composition. Human RBCs were collected into a sucrose/Sorensen's buffer containing heparin (100 Units/ml; "sucrose/Sorensen's/heparin solution"). The cells were centrifuged, the supernatant decanted, and the pellet was placed on ice. Aliquots of the ice cold cell suspension (100 μl) were added to tubes with an equal volume of an ice cold solution containing 40% PEG 3350 daltons with either 0%, 1%, 5% or 10% 1-butanol for final butanol concentrations of 0, 0.5, 2.5 or 5% v/v, respectively. After 5 minutes on ice, the samples were frozen in a thin layer. The frozen samples were transferred to a lyophilizer and freeze-dried until dry (vacuum operating at 100 microns of Hg).

The samples were stored at room temperature in unsealed vials. After 4 hours, each sample was rehydrated with a reagent for measuring oxyHb and lysed with a non-ionic detergent. The lysates were analyzed for percent oxyHb relative to a control blood sample which was not freeze-dried. Illustrated in Table 8 is the effect of various concentrations of 1-butanol on lyophilization of RBCs.

TABLE 8

| Final 1-Butanol Conc. (%) | % oxyHb Recovery |
|---|---|
| 0 | 43 |
| 0.5 | 43 |
| 2.5 | 40 |
| 5.0 | 86 |

The results indicate that oxyHb recovery of freeze-dried RBCs is enhanced when the composition contains 1-butanol for a final concentration of about 5% v/v. As opposed to the dose-related protecting effect observed when DMSO is included as a component in the composition, 1-butanol appears to require a threshold concentration below which little or no protection is observed.

EXAMPLE 9

A Combination Comprising DMSO and 1-butanol as the Organic Solvent in the Composition In one preferred embodiment of the invention, the organic solvent contained in the composition according to the present invention comprises a combination of DMSO and 1-butanol. Experiments were performed to demonstrate whether the protecting effects afforded by 1-butanol or by DMSO are additive. That is, whether the composition according to the present invention is improved if it contains both 1-butanol and DMSO. For this experiment, blood was collected into a sucrose/Sorensen's/heparin solution. The cells were centrifuged, the supernatant decanted, and the pellet was placed on ice. Two 150 µl aliquots were transferred to separate vials and stored in hydrated form for 5 days; one was maintained at 4° C. and the other at room temperature. Four additional aliquots of the ice cold cell suspension were added to tubes containing an equal volume of an ice cold solution containing 40% PEG 3350 daltons w/v with DMSO at either 0 or 5% v/v and/or 1-butanol at either 0 or 10% v/v. After 5 minutes on ice, the samples were placed in a freezer (−70° C.) and frozen in a thin layer. The frozen samples were lyophilized until dry (vacuum operating at 100 microns of Hg).

The dry samples were sealed under vacuum and stored at 25° C. for 5 days. After 5 days, the four dry samples and the two hydrated samples were each brought up to 2.5 ml with a reagent for measuring oxyHb and lysed with a non-ionic detergent. The lysates were analyzed for percent oxyHb relative to a control sample which was not freeze-dried and was analyzed immediately. Illustrated in Table 9 is the effect of various combinations of 1-butanol and DMSO on lyophilization of RBCs.

TABLE 9

| Sample | Storage Temp. | Final 1-Butanol Conc. (%) | Final DMSO Conc. (%) | % oxyHb Recovery |
| --- | --- | --- | --- | --- |
| Hydrated | 4° C. | — | — | 91 |
| Hydrated | 25° C. | — | — | 31 |
| Freeze-dried | 25° C. | 0.0 | 0.0 | 31 |
| Freeze-dried | 25° C. | 5.0 | 0.0 | 33 |
| Freeze-dried | 25° C. | 0.0 | 2.5 | 91 |
| Freeze-dried | 25° C. | 5.0 | 2.5 | 98 |

As consistent with the results illustrated in Tables 6–8, the results here indicate that the biological function of freeze-dried RBCs is improved when the composition contains either 1-butanol or DMSO. However, the results of these experiments also show that when the organic solvent present in the composition comprises a combination of 1-butanol and DMSO, the viability of the RBCs is improved when freeze-dried according to the method of the present invention. For best protection, both of these organic solvents should be present such that the final concentration of organic solvent in the composition is from about 1% to about 20% v/v, with a preferred concentration of from about 5% to about 15% v/v. While hydrated blood cells lost oxyHb content when maintained at 4° C., lyophilized RBCs retained virtually all oxyHb content at room temperature. This unexpected result indicates that when RBCs are freeze-dried using the composition and method according to the present invention, the freeze-dried RBCs outperform hydrated blood over time; and the freeze-dried RBCs are tremendously more resistant to elevated temperatures relative to hydrated RBCs (3-fold higher oxyHb content after 5 days at room temp.).

EXAMPLE 10
Long Term Storage Following Freeze-Drying

For lyophilized RBCs to be practically useful as a source of transfusable red blood cells, the lyophilized RBCs must demonstrate toleration to various storage temperatures, and also exhibit an extended shelf-life (long term storage). As illustrated in Example 9, RBCs freeze-dried using the composition and method according to the present invention are particularly resistant to elevated temperatures which would likely be encountered during storage. Further experiments were performed to demonstrate the stability of freeze-dried RBCs' biological function upon extended storage at an elevated temperature.

Red blood cells were collected into a sucrose/Sorensen's/heparin solution. The cells were centrifuged, the supernatant decanted, and the pellet was placed on ice. An aliquot of the blood suspension (150 µl) was added to a tube containing an equal volume of an ice cold solution containing 40% PEG 3350 daltons with 10% 1-butanol v/v and 5% DMSO v/v. After 5 minutes on ice, the sample was placed in a freezer (−70° C.) and frozen in a thin layer. The frozen sample was lyophilized until dry (vacuum operating at 100 microns of Hg).

The dry sample was sealed under vacuum and stored at the elevated temperature of 25° C. for 23 days. After 23 days, the sample was brought up to 2.5ml with a reagent for measuring oxyHb and lysed with a non-ionic detergent. The lysate was evaluated with an analyzer to determine the following statistics: p50 value and Hill coefficient. The p50 value is an expression of oxygen carrying capacity which relates to the integrity of oxyHb. A Hill coefficient, used in this context, relates to hemoglobin's oxygen binding saturation kinetics. Thus, both measurements are additional indicators of red blood cell viability following lyophilization and reconstitution. These same measurements were taken originally on 150 µl control blood lysate which was not freeze-dried. Illustrated in Table 10 is the effect of extended storage at an elevated temperature on the stability of a reconstituted RBCs' biological function following lyophilization with the composition and method according to the present invention.

TABLE 10

| Sample | Storage Temp. | Storage Time (days) | Hill Coefficient | p.50 |
| --- | --- | --- | --- | --- |
| Control | — | — | 2.76 | 12.76 |
| Freeze-dried | 25° C. | 23 | 2.72 | 12.72 |

The correspondence between the Hill coefficient and p50 values of these two samples indicates that RBCs lyophilized with the composition and method according to the present invention can be stored for considerable lengths of time at an elevated temperature with no significant degradation to its Hb-$O_2$ binding character.

EXAMPLE 11
Rehydration Procedures

For lyophilized RBCs to be practically useful as a source of transfusable red blood cells, the lyophilized RBCs must also demonstrate the ability to be reconstituted in a solution, such as serum, to show that such red blood cells have maintained sufficient integrity to survive the osmotic conditions encountered in vivo. Demonstrated are procedures which may be required to reconstitute freeze-dried RBCs such that high cell recovery is obtained, and high cell integrity is maintained.

Human red blood cells were collected into a sucrose/Sorensen's/heparin solution and centrifuged to concentrate the cells. The supernatant was decanted and the pellet of cells was placed on ice. A small volume of fluorescent labelled-yeast particles was added to serve as an internal standard for evaluating cell recovery. A 0.5 ml aliquot of the RBC/yeast suspension was added to a vial containing 0.5 ml of an ice cold solution containing 40% PEG 3350 daltons with 10% 1-butanol and 5% DMSO. After 5 minutes on ice, the sample was frozen in a uniform thin layer and transferred to a lyophilizer operating at 100 microns Hg. The sample was lyophilized until dry, sealed under vacuum, and stored at 4° C.

To determine the effectiveness of various reconstitution buffers, fractions of the dry sample were rehydrated with one each of the following solutions (at 4° C.): 15% PEG 3350 daltons; 15% PEG 3350 daltons+50 units heparin/ml; 15% PEG 3350 daltons+500 units heparin/ml; 0.9% NaCl; Alsever's buffer; PBS-proper; 145 mM NaCl+5mM KCl +5mM glucose; 0.2M sucrose prepared with Sorensen's buffer; or fetal bovine serum. Cell recovery was determined with a flow cytometer by comparing the RBC/yeast ratio of each sample relative to a control (untreated) cell/yeast suspension. Illustrated in Table 11 is the effect of various reconstitution buffers on the stability of a reconstituted RBCs' integrity following lyophilization with the composition and method according to the present invention.

TABLE 11

| Initial Rehydration Solution | Cell Recovery (%) |
| --- | --- |
| 15% PEG3350 | 99 |
| 15% PEG3350 + 50 U heparin/ml | 98 |
| 15% PEG3350 + 500 U heparin/ml | 93 |
| sucrose/Sorensen's | 2 |
| 0.9% NaCl | <1 |
| NaCl/KCl/glucose | <1 |
| Alsever's | <1 |
| PBS-proper | <1 |
| fetal bovine serum | <1 |

As indicated by the results illustrated in Table 11, high cell recovery upon reconstitution is evident only when the initial rehydration solution contains a threshold level of a high molecular weight hydrophilic polymer such as PEG 3350 daltons. Effective solutions in a range-of 5% to 25% such as 15% PEG 3350 daltons presumably provide conditions whereby cells are allowed to rehydrate while preventing PEG from rapidly disassociating and effluxing from the cells' membranes.

While these data indicate that freeze-dried RBCs can be recovered at high yields when initially rehydrated with PEG solutions, such cells are not transfusion-ready. Experiments have indicated that at this stage, RBCs are not stable and lyse when they come into contact with blood serum. However, such RBCs can be stabilized for re-infusion into the blood by use of a washing procedure which effectively controls the disassociation and efflux of the hydrophilic polymer from the RBC membranes.

To illustrate this embodiment, freeze-dried human RBC/yeast material was rehydrated with a cold solution of 15% PEG 3350 daltons. Aliquots of this suspension (100 μl) were transferred to tubes on ice. To control and slow the rate at which PEG disassociates and effluxes from the RBC membranes, the samples were placed on ice and slowly diluted. Specifically, at 10 minute intervals, the volume in each tube was doubled three times with one each of the following 4° C. solutions (each supplemented with 100 units heparin/ml): 0.9% NaCl; Alsever's buffer; PBS-proper; 145 mM NaCl+5 mM KCl+5mM glucose; 0.2M sucrose prepared with Sorensen's buffer; or fetal bovine serum. Cell recovery values were determined with a flow cytometer by comparing the RBC/yeast ratio of each sample relative to a control (untreated) cell/yeast suspension. Illustrated in Table 12 is the effect of this washing procedure on RBC stabilization.

TABLE 12

| Diluent (+100 U heparin/ml) | Cell Recovery(%) |
| --- | --- |
| NaCl/KCl/glucose | 90 |
| sucrose/Sorensen's | 28 |
| 0.9% NaCl | 3 |
| Alsever's | 3 |
| PBS-proper | <1 |
| fetal bovine serum | <1 |

The high cell recovery value of the cold NaCl/KCl/glucose solution relative to each of the other diluents suggests that a slow washing procedure with specific salt and sugar concentrations is required at this stage of the reconstitution procedure.

In one mode of this embodiment, a washing solution consisting of NaCl/KCl/glucose can be used to dilute and wash PEG from freeze-dried RBCs and prepare cells for contact with blood serum. For this experiment, freeze-dried human RBC (with added yeast particles as a control) was rehydrated with 1 ml of a cold solution of 15% PEG 3350 daltons. After 10 minutes on ice, 1 ml of a cold solution containing 145 mM NaCl+5 mM KCl+5mM glucose+100 units heparin/ml was added to the cell suspension. After 10 more minutes on ice, 2 ml of the same diluent solution was added; after an additional 10 minutes a 4 ml volume of the diluent was added. In this manner, the PEG concentration was slowly reduced to less than 2.5% A small volume of the cell suspension was removed for flow cytometric analysis. The remaining fraction of the cell suspension was centrifuged in a table top centrifuge at approximately 1600×g for 5 minutes. The supernatant was decanted and the pellet was tapped. A small volume of these cells was removed and analyzed with the flow cytometer. To the remaining 200l of high density, washed RBCs, 600 μl of room temperature fetal bovine serum was added. These cells were analyzed with the flow cytometer. The recovery data corresponding to the different aliquots taken throughout this washing procedure are presented in Table 13 below.

TABLE 13

| Washing Procedure | Cell Recovery(%) |
| --- | --- |
| Cells rehydrated with 15% PEG3350 and diluted 3 times with NaCl/KCl/glucose | 96 |
| diluted cell suspensions centrifuged | 89 |
| fetal bovine serum added to washed cells | 87 |

Thus, using a washing procedure which effectively controls the disassociation and efflux of the hydrophilic polymer from the RBC membranes, RBCs which have been lyophilized using the composition and method according to the present invention can be reconstituted and be stabilized in a transfusable form. One such washing procedure is illustrated which is based on initial rehydration with a hydrophilic polymer-containing solution, followed by dilution with a cold solution of NaCl/KCl/glucose.

From the foregoing description, one skilled in the art of freeze-drying will be capable of lyophilizing mammalian RBCs in a manner which is compatible with high cell recovery and biological activity following rehydration. Obvious modifications and variations, such as substitution of equivalents, will be apparent to one skilled in the art from the foregoing description, and such are considered within the scope of the claimed invention.

What is claimed is:

1. A composition for lyophilizing mammalian red blood cells comprising in a solution:
   a hydrophilic polymer having a molecular mass of from about 1,450 to about 20,000 daltons in a concentration of from about 5% to about 50% w/v;
   a carbohydrate selected from the group consisting of at least one monosaccharide, a disaccharide, and a combination thereof, said carbohydrate is present in the solution in a concentration of from about 0.01M to about 0.2M; and
   an organic solvent selected from the group consisting of a primary alcohol, a secondary alcohol, dimethyl sulfoxide, and a combination thereof, wherein the organic solvent is in a concentration range of from about 0.5% to about 20% v/v.

2. The composition according to claim 1, wherein the hydrophilic polymer is selected from the group consisting of polyethylene glycol, dextran, hydroxyethyl starch, and polyoxyethylene-23-lauryl ether.

3. The composition according to claim 1, wherein the carbohydrate is selected from the group consisting of sucrose, glucose, and fructose.

4. The composition according to claim 1, wherein the organic solvent is selected from the group consisting of 1-butanol, dimethyl sulfoxide, and a combination thereof.

5. The composition according to claim 1, further comprising a component selected from the group consisting of a salt low in chloride ions, an antiaggregant, and a combination thereof, useful for lyophilizing mammalian red blood cells at relatively high cell densities.

6. The composition according to claim 5, wherein the salt is a salt selected from the group consisting of $KH_2PO_4$, $Na_2HPO_4$, and a combination of $KH_2PO_4$ and $Na_2HPO_4$ in a final concentration of from about 5 mm to about 150 mM.

7. The composition according to claim 5, wherein the anti-aggregant is an anticoagulant selected from the group consisting of CPD in a concentration of from about 5% to about 15% v/v, CPD-A in a concentration of from about 5% to about 15% v/v, and heparin in a concentration from about 10 to about 1000 USP units/ml.

8. A composition for lyophilizing mammalian red blood cells comprising in a solution:
   a hydrophilic polymer having a molecular mass of from about 1,450 to about 20,000 daltons in a concentration of from about 5% to about 50% w/v;
   a carbohydrate comprising a disaccharide which is present in the solution in a concentration of from about 0.01M to about 0.2M; and
   an organic solvent selected from the group consisting of a primary alcohol, a secondary alcohol, dimethyl sulfoxide, and a combination thereof, wherein the organic solvent is in a concentration range of from about 0.5% to about 20% v/v.

9. The composition according to claim 8, wherein the hydrophilic polymer is selected from the group consisting of polyethylene glycol, dextran, hydroxyethyl starch, and polyoxyethylene-23-lauryl ether.

10. The composition according to claim 8, wherein the disaccharide is sucrose.

11. The composition according to claim 8, wherein the organic solvent is selected from the group consisting of 1-butanol, dimethyl sulfoxide, and a combination thereof.

12. The composition according to claim 8, further comprising a component selected from the group consisting of a salt low in chloride ions, an antiaggregant, and a combination thereof, useful for lyophilizing mammalian red blood cells at relatively high cell densities.

13. The composition according to claim 12, wherein the salt is a salt selected from the group consisting of $KH_2PO_4$, $Na_2HPO_4$, and a combination of $KH_2PO_4$ and $Na_2HPO_4$ in a concentration of from about 5 mM to about 150 mM.

14. The composition according to claim 12, wherein the anti-aggregant is selected from the group consisting of CPD in a concentration of from about 5% to about 15% v/v, CPD-A in a concentration of from about 5% to about 15% v/v, and heparin in a concentration from about 10 to about 1000 USP units/ml.

15. A method for making lyophilized mammalian red blood cells comprising the steps of:
   (a) mixing mammalian red blood cells in the composition according to claim 1;
   (b) chilling the mixture of step (a) for a time sufficient to allow the composition to interact with cell membranes and hemoglobin of said red blood cells;
   (c) freezing the mixture; and
   (d) lyophilizing the mixture by removing water from the mixture by sublimation.

16. A method for making lyophilized mammalian red blood cells comprising the steps of:
   (a) mixing mammalian red blood cells in the composition according to claim 5;
   (b) chilling the mixture of step (a) for a time sufficient to allow the composition to interact with cell membranes and hemoglobin of said red blood cells;
   (c) freezing the mixture; and
   (d) lyophilizing the mixture by removing water from the mixture by sublimation.

17. A method for making lyophilized mammalian red blood cells comprising the steps of:
   (a) mixing mammalian red blood cells in the composition according to claim 8;
   (b) chilling the mixture of step (a) for a time sufficient to allow the composition to interact with cell membranes and hemoglobin of said red blood cells;
   (c) freezing the mixture; and
   (d) lyophilizing the mixture by removing water from the mixture by sublimation.

18. A method for making lyophilized mammalian red blood cells comprising the steps of:
   (a) mixing mammalian red blood cells in the composition according to claim 10;
   (b) chilling the mixture of step (a) for a time sufficient to allow the composition to interact with cell membranes and hemoglobin of said red blood cells;
   (c) freezing the mixture; and
   (d) lyophilizing the mixture by removing water from the mixture by sublimation.

19. A method for making lyophilized mammalian red blood cells comprising the steps of:
   (a) mixing mammalian red blood cells in the composition according to claim 12;
   (b) chilling the mixture of step (a) for a time sufficient to allow the composition to interact with cell membranes and hemoglobin of said red blood cells;
   (c) freezing the mixture; and
   (d) lyophilizing the mixture by removing water from the mixture by sublimation.

* * * * *